| United States Patent [19] | [11] Patent Number: 5,026,728 |
| Kendall et al. | [45] Date of Patent: Jun. 25, 1991 |

[54] TREATMENT OF ARTHRITIS AND INFLAMMATION USING N,N-DIMETHYLGLYCINE

[75] Inventors: Roger V. Kendall, Williston, Vt.; John W. Lawson, Clemson, S.C.

[73] Assignee: Foodscience Corporation, Essex Junction, Vt.

[21] Appl. No.: 416,788

[22] Filed: Oct. 5, 1989

[51] Int. Cl.⁵ .......................................... A61K 31/195

[52] U.S. Cl. .................................................... 514/561
[58] Field of Search ........................................ 514/561

*Primary Examiner*—Stanley J. Friedman
*Attorney, Agent, or Firm*—Millen, White & Zelano

[57] ABSTRACT

This invention relates to a method for treating arthritis and other systemic inflammatory conditions by treating the patient systemically with N,N-dimethylglycine.

8 Claims, No Drawings

TREATMENT OF ARTHRITIS AND INFLAMMATION USING N,N-DIMETHYLGLYCINE

BACKGROUND OF THE INVENTION

This invention relates to the use of N,N-dimethylglycine (DMG) to treat arthritis and inflammation in man or animals.

Dimethylglycine is an intermediary metabolite and amino acid found in low levels in many foods, and is produced in the body from choline. DMG is an endogenous compound and an enzyme system in the body effectively converts the substance into metabolites that are either used by the body or are safely excreted from the body.

A great deal of research has been carried out in recent years on the physiological effects of N,N-dimethylglycine.

Referring to previous work, U.S. Pat. No. 4,385,068, issued May 24, 1983, discloses treating irradiated animals with a derivative of this compound to alleviate the effects of excess radiation on the immune system. The stated object of the invention of U.S. Pat. No. 4,385,068 is (a) to provide a method to enhance one or both of the cell-mediated response and humoral response of the body; (b) provide a method whereby the deliberately induced production of antibody artificially acquired in a living organism can be enhanced, and (c) to provide a method to increase the amount of antibody production and/or decrease the time of antibody production in the deliberately induced production of antibodies in a living organism. According to the patent, the DMG is administered so that the immunological response of the living organism is potentiated when exposed to an antigen in a natural environment and/or when deliberately exposed, or exposed to a subject after the subject has been exposed to a disease agent having an antigenic component in a natural environment in order to aid the host in responding to the naturally occurring infection.

The literature is also replete with articles concerning N,N-dimethylglycine and its potential uses.

At the 1980 Pacific Slope Biochemical Conference a paper entitled "Decrease of Lactic Acid Concentration in Blood of Animals Given N,N-Dimethylglycine" was presented. This research gave the nutritional evaluation as a result of a 157-day subchronical estimation of N,N,-dimethylglycine toxicity. This study also indicated that a decreased lactic acid production by male New Zealand white rabbits exposed to severe surgical stress by administering intravenously dimethylglycine. High-dose rats showed better adaptation to hypoxia subchronical toxicity tests.

In the January, 1981 issue of The Journal of Infectious Diseases, Vol. 143, No. 1, an article entitled "Immunomodulating Properties of Dimethylglycine in Humans", discussed the fact that dimethylglycine is an immunomodulator, if not an immunoadjuvant in humans (since the latter term is reserved for parenterally administered substances that are incorporated or injected simultaneously with an antigen). The normalization of mitogenic responsiveness by lymphocytes from patients with sickle cell disease and diabetes was tested. In both groups, the blast transformation activity of lymphocytes treated with DMG and exposed to three lectins was approximately doubled. Preliminary data suggest, according to the authors, that DMG is both a humoral and cellular immunomodulator, and might have great use with vaccines for intracellular infections and certain parasitic diseases.

The March, 1982 issue of Equine Practice contains an article entitled "Effect of a Nutritional Supplement Containing N,N-Dimethylglycine (DMG) on the Racing Standardbred." This article discloses that research showed that DMG can increase oxygen utilization and thereby decrease lactic acid levels in animals under extreme stress. The article also discusses the finding that human tests indicated an increase in exhaustion time, and an enhancement of the body's immune response, both by increasing the antibody production and lymphocyte generation by the administration of DMG. The tests reported in this article indicated that the inclusion of DMG in the diet of the racing Standardbred is responsible for a lower blood lactic acid level following training. Trainers found the horses to be more aggressive, to have better appetites and attitudes and to recover faster from racing and training than the controls.

The November-December, 1982 issue of Canine Practice contains an article entitled "A Clinical Evaluation of N,N-Dimethylglycine (DMG) and Diisopropylammonium Dichloroacetate (DIPA) on the Performance of Racing Greyhounds". This article summarized the biological reactions of dimethylglycine in three broad categories: transmethylation, cellular respiration, and hepatic function. The study that was the subject of the article indicated that improvement in racing performance was found when greyhounds were given DMG, and also stated that they showed better recovery after races with less fatigue or muscle stiffness. Additional clinical applications of DMG, including exertional rhabdomyolysis (inflammatory change in the muscle fibers of the longissimus group), muscular cramp, and hepatopathology were discussed.

In the February, 1987 issue of Let's Live magazine, an article entitled "DIMETHYLGLYCINE UPDATE, New Studies Confirm DMG Improves Health" states that the benefit of enhanced immunity is protection against diseases ranging from and AIDS to minor diseases such as influenza. The article states that DMG is a metabolic enhancer, acts as a detoxifying agent and antioxidant, and is a versatile normalizer of physiological functions. The article also discusses the fact that the immune system is a complex network of white blood cells and molecular compounds, such as antibodies and interferon. There are two types of white blood cells-lymphocytes and macrophages. The immune system produces three types of lymphocytes: T cells, B cells, and K cells. Interferon is an antiviral, antitumor compound produced from T cells. The article indicates that T cells identify and reject foreign matter, while B cells produce antibodies. The article states that little is understood about the killer K cells, which can attack tumor cells directly. The article further states that early research showed that DMG stimulates B cells to produce much higher antibody responses (humoral branch) and potentiates the activity of T cells and macrophages (cellular immunity branch).

The article also states that the DMG was effective in doubling interferon production, and that further work is underway to evaluate DMG's effect on K cells, the body's principal defense mechanism against tumor cells. The article also alludes to a related line of research which indicated that the methyl-group donating ability of DMG is protective against cancer.

In the February, 1987 issue of Health Consciousness, an article entitled "N,N-Dimethylglycine and the Immune Response" reviewed the prior research in the effect of DMG on the body, and also indicated that DMG will increase interferon production. The article states that DMG is an oral immune stimulating nutrient which can offer individuals increased resistance to and recovery from infectious diseases, and stated that depressed immunity is associated with most degenerative diseases such as cancer, diabetes and cardiovascular disease.

At the 1987 ASM Annual Meeting, a paper entitled "The Effect of DMG on the Immune Response of Rabbits" was presented. This paper concluded that DMG can affect the cellular branch of the immune system by lymphocyte activation. Lymphocytes from DMG-fed animals can stimulate the cellular immune system by lymphatic proliferation. During primary response, high levels of interferon was present in the DMG fed animals, regardless of the immunogen source. No interferon was detected in immunized control animals not fed DMG. Interferon was not present in samples obtained following the secondary response.

In an article entitled "DMG, Properties and Proprieties" published in The Blood Horse on June 27, 1987, research on humans Was discussed Which showed that DMG stimulated B-cells produce much higher antibody responses and that it also enhances the activity of T cells and macrophages.

Type II collagen has been shown to induce an arthritis in rats similar to rheumatoid arthritis in humans. However, Types I and III collagens have no arthritogenic capabilities (Trentham, D. E. et al., J. Exp. Med. 146, 857 [1977] and Andriopoulos, N. A., et al., Arthritis Rheum. 19, 613 [1976]). In rats susceptible to collagen induced arthritis, e.g., outbred Wistar Sprague-Dawley and inbred Wistar-Lewis, arthritis can also be induced by using *Mycobacterium butyricum* in complete Freund's adjuvant (Pearson, C. M. et al., Am. J Pathol. 42, 73–95 [1963]). This adjuvant arthritis produces antibodies that cross-react with Type II collagen (Trentham, D. E. et al., J. Clin. Invest. 66, 1109–1117 [1980]).

N,N-dimethylglycine (DMG) has been demonstrated to be an effective immunomodulator in humans by way of the cellular and humoral immune system. It has now been found that DMG is an effective agent for the treatment of systemic inflammatory ailments generally, and more particularly, for the treatment of arthritis.

OBJECTS OF THE INVENTION

It is an object of this invention to provide a method of treating arthritis.

It is another object of this invention to provide a method for treating systemic inflammatory ailments.

It is yet another object of this invention to provide a method for treating autoimmune diseases.

SUMMARY OF THE INVENTION

The above and other objects are obtained by administering N,N-dimethylglycine to an animal suffering from an inflammatory ailment in an amount sufficient to ameliorate the inflammatory condition.

In one aspect, this invention relates to a method of ameliorating the inflammation associated with arthritis, comprising administering to a patient afflicted with arthritis an amount of N,N-dimethylglycine or a pharmaceutically acceptable salt thereof effective to ameliorate the inflammation.

In another aspect, this invention relates to a method of treating systemic inflammatory ailments, comprising administering to a patient in need of such treatment an amount of N,N-dimethylglycine or a pharmaceutically acceptable salt thereof effective to treat the inflammation.

In yet another aspect, this invention relates to a method of treating autoimmune diseases, comprising administering to a patient in need of such treatment an amount of N,N-dimethylglycine or a pharmaceutically acceptable salt thereof effective to treat the disease.

Upon further study of the specification and appended claims, further objects and advantages of this invention will become apparent to those skilled in the art.

DETAILED DESCRIPTION OF THE INVENTION

It has now been found that N,N-dimethylglycine (DMG), a compound of the formula:

$$(CH_3)_2NCH_2COOH$$

or a pharmacologically acceptable salt thereof, can be used to treat arthritis, whereby DMG can help reduce the swelling and inflammation associated therewith.

DMG has been demonstrated to effectively modulate the cellular and humoral immune system in humans. Rheumatoid arthritis is known to be a disease of altered immunity. However, it was not known what effect, if any, would be expected for DMG administered as an antiarthritic or antiinflammatory treatment.

In in vitro cell cultures of hybridoma antibody producing cells, it has been demonstrated that DMG increases the production of antibodies. However, since rheumatoid arthritis, inflammation and autoimmune diseases have in common an increased, pathological immune response, it was not possible to predict whether treatment with DMG would be beneficial, neutral, or harmful to patients, if administered to prevent or treat these conditions.

Arthritis in its generic sense refers to any abnormality of a joint in which objective findings of heat, redness, swelling, tenderness, loss of motion or deformity are present. The term is usually qualified by an adjective describing the cause, such as rheumatoid, gouty, infectious or post-traumatic. Rheumatoid arthritis is a common form of chronic inflammatory arthritis. It is a multisystem disease of unknown cause, and is associated with the presence of autoantibodies to IgG. In addition, antibodies to collagen have been detected in humans with rheumatoid arthritis (Andriopoulos, N. A., et al., Arthritis Rheum. 19, 613 (1976).

Inflammation is the localized response of vascularized tissues to injury caused by chemical, physical or biological agents. Clinically, the signs of inflammation include redness, swelling, heat, pain, loss of function and fever. Immune inflammation is inflammation resulting from an immune response.

Autoimmune diseases involve host immune reactions to autoantigens. Autoantibodies at cell receptors may produce disease by agonist activity (as the antibody to thyrotrophin receptors in thyrotoxicosis) or by antagonist activity (as the antibody to acetylcholine receptors in myasthenia gravis). Immune complexes of non-organ-specific autoantigens and autoantibodies can give rise to glomerulonephritis and vasculitis, as occurs in systemic lupus erythematosus. Organ-specific autoantibodies may cause the destruction of the relevant cells if the antigens occur on cell or basement membranes. Thus autoantibodies to thyroid cells, adrenal cells, and the parietal cells of the stomach are implicated, respectively, in Hashimoto's disease, Addison's disease and pernicious anemia. Autoantibodies to basement membrane give rise to the Goodpasture syndrome. Cellular immune reactions against autoantigens can be seen in experimental allergic encephalomyelitis and are believed to be similarly responsible for some forms of human encephalomyelitis.

Injection of Type II collagen into rats has been demonstrated to be an experimental animal model for human rheumatoid arthritis (Stuart, J. M. et al., J. Exp. Med. 155, 1 [1982]). Collagen II arthritis shares several features in common with human rheumatoid arthritis, including inducing a chronic inflammatory swelling at joints near the situs of injection; e.g., injection in the hind footpad of a rat causes swelling at, e.g., the proximal ankle joint. Histological features include synovial proliferation, mononuclear cell infiltration, fibrin deposition and pannus formation resulting in damage to cartilage and subchondrial bone. Serologically there is an invariable association of arthritis with high antibody levels to collagen, and serum from immunized animals can transfer arthritis to non-immunized recipients.

It has now been shown that if DMG is administered daily, starting on day 14 prior to injection with Type II collagen at dosages sufficient to induce arthritis, at a DMG dosage of 100 mg/kg/day, the characteristic inflammation and swelling associated with Type II collagen-induced arthritis either does not develop to the same extent, or does not develop at all.

DMG is a relatively non-toxic substance. It was found by researchers that in the rat, DMG-HCl has an acute $LD_{50}$ toxicity when administered orally as a neutralized aqueous solution of 7.4 g/kg of body weight; 6 g/kg when administered intraperitoneally, and 5.4 g/kg when administered subcutaneously in mice (Jerzy W. Medusky, Abstract, Pacific Slope Biochemical Conference, U.C. San Diego, Calif., July, 1980).

The instant invention involves the administration of DMG or a pharmaceutically acceptable salt thereof to an animal, including but not limited to mammals, e.g., humans, horses and household pets.

One aspect of this invention involves administering dimethylglycine to a patient, e.g., a human, who has been diagnosed as having arthritis. Animals, such as dogs, horses, etc. and human patients suffering from various stages of acute or chronic arthritic disease, characterized by inflammation of one or more joints, pain, immobilization, swelling and changes in joint structures can benefit from orally administered DMG for the amelioration of symptoms. Rheumatoid, gouty, infectious and posttraumatic arthritis can be treated by administration of DMG.

Other systemic inflammatory conditions of various body tissues including conjunctivitis, dermatitis, bronchitis, rhinitis, etc. brought about by injury, allergies, infections, microorganisms, trauma and chemical and physical agents are also relieved by the administration of DMG.

DMG is also active as an intramuscular injection. Clinical experience indicates that DMG will not interfere with most other drug therapies generally and can be given to patients regardless of age, sex, or general health status either by oral, IM or IV routes.

In another aspect of this invention, a patient, e.g. human, who is known to be susceptible to arthritis may be treated with DMG to prevent the formation of the disease. Such a patient may be one who is known to be susceptible to arthritis, e.g. those who have a family history of the disease, or who have had repeated or severe joint injuries.

The DMG used in the instant invention can be processed in accordance with conventional methods of galenic pharmacy to produce medicinal agents for administration to patients, e.g. mammals, including humans.

The DMG used in this invention can be employed in admixture with conventional excipients, i.e. pharmaceutically acceptable organic or inorganic carrier substances suitable for parenteral, enteral (e.g., oral) application which do not deleteriously react with the active compound. Suitable pharmaceutically acceptable carriers include but are not limited to water, salt solutions, alcohols, gum arabic, vegetable oils, benzyl alcohols, polyethylene glycols, gelatine, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g. lubricants, preservatives, stabilizers, wetting agents emulsifiers, salts for influencing osmotic pressure, buffers, coloring, flavoring and/or aromatic substances and the like which do not deleteriously react with the active compound. They can also be combined where desired with other active agents.

For parenteral application, particularly suitable are injectable, sterile solutions, preferably oily or aqueous solutions, as well as suspensions, emulsions, or implants. Ampoules are convenient unit dosages.

For enteral application, particularly suitable are tablets, dragees, liquids, drops, or capsules.

Generally, when used in the treatment of or the prevention of arthritis, or in the treatment of inflammation, the compounds of this invention are dispensed in unit dosage form comprising 1-100 mg/kg, preferably 20-80 mg/kg in a pharmaceutically acceptable carrier per unit dosage.

The daily dosage of the compounds according to this invention, when used to treat or prevent arthritis or treat inflammation, is generally about 1-500 mg/kg/day, preferably 10-100 mg/kg/day. When administered orally, the dosage can be in a single or divided dosages every 2-24 hours, preferably every 4 hours; when administered intraperitoneally or intramuscularly initially it should be administered daily, and thereafter periodically, preferably at least every third day. Arthritic conditions in humans, such as osteoarthritis, gouty arthritis and rheumatoid arthritis, are all benefitted by the daily intake of, for example, from 250 to 2,000 mg of DMG taken in divided doses. When used as part of a prevention or maintenance program in humans, DMG can be administered in dosages of, for example, from 100 to 400 mg/day.

DMG is administered analogously for the treatment of other inflammatory conditions as well.

DMG has also been shown to be useful in the treatment of diseases of veterinary animals, including horses, having inflammatory conditions. For example, chronic obstructive pulmonary disease (heaves or chronic alveolar emphysema), which is a chronic noninfectious respiratory disease of horses, characterized by labored respirations, chronic cough, unthriftiness and lack of stamina, has been successfully treated with DMG. This respiratory condition is thought to be allergy related and is accompanied by inflammation and narrowing of the airway passages in the lungs. DMG was demonstrated to reduce the inflammatory condition and to be an effective therapy for heaves in horses.

DMG can be administered concurrently or alternately with other therapeutic treatments conventionally employed in arthritis or inflammation therapy, e.g. aspirin and steroids as well as other acceptable therapies designed to reduce inflammation and treat arthritis.

It will be appreciated that the actual preferred amounts of active compound in a specific case will vary according to the particular compositions formulated, the mode of application, and the particular situs and organism being treated. Dosages for a given host can be determined using conventional considerations, e.g., by customary comparison of the differential activities of the subject compounds and of a known agent, e.g., by means of an appropriate, conventional pharmacological protocol.

It will also be appreciated that DMG is also useful for the treatment of autoimmune diseases, using the above-described protocol and dosages. For example, a patient who has a family history of autoimmune disease, or who is at high risk for contracting such as disorder or who has been diagnosed as having an autoimmune dysfunction in which the immune response of the individual responds to his body's own components can be treated with DMG to either prevent the onset of the disease or as therapy for the disease.

Without further elaboration, it is believed that one skilled in the art can, using the preceding description, utilize the present invention to its fullest extent. The following preferred specific embodiments are, therefore, to be construed as merely illustrative, and not limitative, of the remainder of the disclosure in any way whatsoever.

In the foregoing and in the following examples, all temperatures are set forth uncorrected in degrees Celsius and, unless otherwise indicated, all parts and percentages are by weight.

The entire texts of all applications, patents and publications, if any, cited above and below, are hereby incorporated by reference.

EXAMPLES

EXAMPLE 1

Demonstration of Induction of Antibodies by Type II Collagen, with and without DMG

Animals

Female Wistar outbred rats (age 10–12 weeks) were obtained from Charles River Breeding Laboratories Inc., Wilmington, Mass.) housed in metal cages and fed standard rodent chow with water ad libitum.

Immunization

Immunization was performed using the method outlined by Stuart et al. (Stuart et al., supra). Type II collagen was dissolved in 0.01N acetic acid at a concentration of 2 mg/ml stirring overnight at 4° C. An emulsion was made using incomplete Freund's adjuvant (Difco) and each collagen solution at a ratio of 6:4. Eighteen Wistar rats were given 0.1 ml of a cold emulsion of collagen II by intradermal injection of the left hind footpad and booster injections in the tail at one week and again on day 36.

Dimethylglycine Administration

Dimethylglycine mixed in distilled water was administered intraperitoneally to half of the rats in the study at a dosage rate of 100 mg/kg body weight per day, beginning on the day of collagen immunization. Control rats were injected with only distilled water. Rats were sacrificed at the time of the occurrence of arthritis and were bled by cardiac puncture. Rats surviving at day 30 were bled by the tail vein and were bled again at the end of the study (day 51).

Arthritis Evaluation

Animals in both groups were observed daily for the onset of arthritis. Swelling of the hindpaws was quantitated by measuring the thickness of the ankle from medial to lateral malleolus with a caliper (as done by Trentham et al. supra). Onset of arthritis was determined to be when the animal no longer placed its weight on the inflamed limb or demonstrated any movement of the joint, i.e., the limb became "locked", and the diameter of the affected joint increased to 2–2½ times the diameter of the unaffected limb.

Immunoassay of Antibody to Collagen

Sera were obtained by cardiac puncture on the day arthritis developed or at the end of the study (day 51). An enzyme-linked immunoassay (ELISA) technique adapted from the methods described by Stuart et al. supra was used to measure antibody titres.

Flat bottom 96 well microtitre plates (Corning) were coated with collagen as follows: Collagen was dissolved in 0.4 ionic strength phosphate buffer, pH 7.6 by stirring overnight at 4° C. The collagen concentration was adjusted to 5 µg/ml determined by the Lowry method (Lowry, O. et al., J. Biol. Chem. 193, 265 [1951]). Each well received 100 µl of collagen solution and the plates were incubated at 4° C. overnight. The coating solution was removed by inverting the plate and sharply snapping the wrist to remove remaining droplets. To reduce nonspecific absorption a blocker of phosphate-buffered saline (PBS) (pH 7.4) containing 0.5% ovalbumin (Grade V), Sigma Chemical Co., St. Louis, Mo.) was added and incubated for 1 hr. The plates were washed with PBS-Tween (containing 2% Tween 20) three times and used immediately. The sera were diluted with PBS-Tween containing 0.5% ovalbumin and aliquots of 100 µl were added to the Type II collagen-coatad microtitre plates. The plates were incubated at 4° C. overnight and washed three times with PBS-Tween. One hundred µl of a 1:3000 dilution of rabbit anti-rat IgG peroxidase conjugate (Sigma) was added and incubated for 4 hr at room temperature. Excess conjugate was removed by washing three times with PBS-Tween and the amount of conjugate bound was determined by adding orthophenylenediamine (OPD) (Sigma Chemical Co.) as a substrate. The substrate was prepared by adding 40 mg of OPD to 1,000 ml of 0.224M citric acid 0.05M dibasic sodium phosphate pH 5.0 and adding 400 µl of 3% hydrogen peroxide. After incubation with the substrate for 20 min the microtitre plates were read for absorbance at 490 nm using a Mini Reader II (Dynatech).

Results

As can be seen from Table 1, rats immunized with Type II collagen and treated with DMG developed higher antibody titres than control animals similarly immunized but not treated with DMG. Higher antibody titres are generally associated with a more severe arthritic response. In general, it was noted that an ELISA reading of greater than 0.6 was associated with arthritic symptoms in the untreated rats. However, in spite of the higher ELISA readings which generally developed in the DMG-treated rats, they did not develop to the same extent the arthritic swellings of the hindpaws typical of the non-DMG-treated group.

TABLE 1

Antibody Titres in Rats Injected with Type II Collagen With and Without Treatment with DMG

| Serum from Rat | ELISA Reading Day | | |
|---|---|---|---|
| | 17 | 30 | 51 |
| Controls | | | |
| A | — | .33 | .26 |
| B | — | .03 | .23 |
| C | — | .28 | .32 |
| D* | — | .09 | — |
| E | — | .08 | .20 |
| F | — | .18 | .17 |
| G* | .10 | — | — |
| H | — | .54 | .54 |
| I | — | .31 | .35 |
| Mean | .10 | .23 | .30 |
| DMG-Treated | | | |
| A* | .78 | — | — |
| B | — | .20 | .90 |
| C | — | .17 | .56 |
| D | — | .48 | .64 |
| E | — | .47 | .60 |
| F | — | .00 | .88 |
| G | — | .28 | .18 |
| H | — | .32 | .18 |
| I | — | .33 | .35 |
| Mean | .78 | .28 | .54 |

*Indicates rats which showed arthritic swelling

EXAMPLE 2

Prevention of Arthritis in Collagen-Injected Rats Treated with DMG

Eighteen rats were divided into two groups. Nine animals were injected i.p. with DMG (100 mg/kg body weight) daily, starting on day 14 prior to administration of collagen II, and continuing for 30 days after collagen II injection or until severe arthritic lesions were observed, if earlier. The remaining nine rats were similarly injected i.p. with sterile water. In this experiment, as compared with Example 1, the source of the collagen II was changed from a commercial preparation (Chemicon Corp., Temecula, Calif.) to a fresh preparation prepared by the process according to Trentham et al., 1977, supra. This preparation of collagen II, when injected into the rats as described above, resulted in a higher and more consistent induction of both the antibody response and the physical manifestations of arthritis.

Results

Under these conditions, of the nine animals receiving DMG, only two developed the characteristic inflammation and swelling to any extent. In contrast, all of the control animals developed the arthritic inflammation and swelling. Seven of these latter animals demonstrated such a severe reaction between days 14–21 post-collagen II injection that they were immediately euthanized to prevent undue suffering.

EXAMPLE 3

Treatment of Rheumatoid Arthritis in Humans by Administration of DMG

Three patients, diagnosed as having rheumatoid arthritis in one or both knees with symptoms of acute pain, inflammation, joint tenderness and morning stiffness, were treated orally with 500 mg of DMG taken four times daily. The test period lasted for six weeks, during which time no other antiinflammatory drugs were taken. After 21 days, two patients reported significant improvement in reduction of inflammation, pain and morning stiffness, and the third patient reported a lesser improvement. All three patients reported less fatigue and less night pain while taking DMG. Additional improvement was noted in all three patients during the last three weeks of therapy.

EXAMPLE 4

Treatment of Gouty Arthritis in Humans by Administration of DMG

DMG was administered to two patients suffering from gouty arthritis, at a dosage of 250 mg t.i.d. over a three week period. Less pain, redness and inflammation were noted. Benefits were noted after 7–10 days, and were maximal after two weeks.

EXAMPLE 5

Treatment of Chronic Obstructive Pulmonary Disease in Horses by Administration of DMG Three standardbred horses, ages 3 to 7 years, were diagnosed as having chronic obstructive pulmonary disease, also known as equine asthma or the heaves. Clinical signs included frequent coughing, nasal discharge, increased respiratory rate and wheezing in the chest area. The horses were treated orally with 1.5 g of DMG hydrochloride twice daily for ten days. All three horses showed symptomatic relief after 5 days, with improved breathing and less nasal discharge, and by the end of 10 days, the air passages of all three horses had cleared.

EXAMPLE 6

Treatment of Systemic Lupus Erythematosus by Administration of DMG

Administer DMG to a patient suffering from systemic lupus erythematosus at a dosage of 500 mg t.i.d. for at least three weeks, or until the condition is ameliorated.

EXAMPLE 7

Prevention of Rheumatoid Arthritis by Administering DMG

Administer DMG to a patient known to be susceptible to rheumatoid arthritis, at a dosage of 500 mg per day, thereby avoiding or ameliorating the development of the condition.

EXAMPLE 8

Treatment of Traumatic Inflammation by Administering DMG

Administer DMG to a patient suffering from an injury and concomitant inflammation, at a dosage of 250 mg t.i.d. per day, for 10 days or until the inflammation is relieved.

The preceding examples can be repeated with similar success by substituting the generically or specifically described coatings of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method of ameliorating the inflammation associated with arthritis, comprising administering to a patient afflicted with arthritis an amount of N,N-dimethylglycine or a pharmaceutically acceptable salt thereof effective to ameliorate the inflammation.

2. A method according to claim 1, wherein the N,N-dimethylglycine is administered systemically.

3. A method according to claim 2, wherein the N,N-dimethylglycine is administered orally.

4. A method according to claim 1, wherein the N,N-dimethylglycine is administered in an amount of 1–500 mg/kg/day.

5. A method according to claim 4, wherein the N,N-dimethylglycine is administered orally.

6. A method of treating systemic inflammation, comprising administering to a patient in need of such treatment an amount of N,N-dimethylglycine or a pharmaceutically acceptable salt thereof effective to ameliorate the inflammation.

7. A method according to claim 6, wherein the N,N-dimethylglycine is administered in a dosage of 1–500 mg/kg.

8. A method according to claim 7, wherein the N,N-dimethylglycine is administered orally.

* * * * *